(12) United States Patent
Heideman

(10) Patent No.: US 8,154,716 B2
(45) Date of Patent: Apr. 10, 2012

(54) WAVEGUIDE-BASED SENSOR

(75) Inventor: Rene Gerrit Heideman, Oldenzaal (NL)

(73) Assignee: Octrolix BV, Enschede (NL)

( * ) Notice: Subject to any disclaimer, the term of this patent is extended or adjusted under 35 U.S.C. 154(b) by 399 days.

(21) Appl. No.: 12/554,721

(22) Filed: Sep. 4, 2009

(65) Prior Publication Data

US 2011/0058158 A1   Mar. 10, 2011

(51) Int. Cl.
  *G01J 1/44* (2006.01)
(52) U.S. Cl. ...................................................... 356/226
(58) Field of Classification Search .................... 356/226
  See application file for complete search history.

(56) References Cited

U.S. PATENT DOCUMENTS

| | | | |
|---|---|---|---|
| 5,262,638 A | 11/1993 | Egalon et al. | |
| 5,809,185 A | 9/1998 | Mitchell | |
| 2005/0002606 A1* | 1/2005 | James et al. | 385/31 |
| 2006/0170931 A1* | 8/2006 | Guo et al. | 356/480 |
| 2007/0230884 A1* | 10/2007 | Minelly et al. | 385/125 |
| 2010/0047919 A1* | 2/2010 | Klunder et al. | 436/172 |

FOREIGN PATENT DOCUMENTS

| WO | 9854573 A1 | 12/1998 |
|---|---|---|
| WO | 03071235 A1 | 8/2003 |

OTHER PUBLICATIONS

Ligler et al., "Integrating Waveguide Biosensor", "Analytical Chemistry XP-001115843", Feb. 1, 2002, pp. 713-719, vol. 74, No. 3, Publisher: American Chemical Society.
Rasmusson, Marcus, "EP Application No. 10175086.7 Extended European Search Report Oct. 24, 2011", , Publisher: EPO, Published in: EP.

* cited by examiner

*Primary Examiner* — Michael P Stafira
(74) *Attorney, Agent, or Firm* — DeMont & Breyer, LLC

(57) ABSTRACT

A sensor for sensing a target chemical with high signal-to-noise ratio is disclosed. In some embodiments, the sensor comprises a sensing region that is optically coupled with an attenuation region. The sensing region receives optical stimulation that comprises light characterized by an excitation wavelength. In response to exposure to the target chemical, the sensing region fluoresces at a fluorescence wavelength. The attenuation region receives light from the fluorescing sensing region that includes light characterized by the fluorescence wavelength (i.e., signal) and light characterized by the excitation wavelength (i.e., noise). The attenuation region conveys the light to a detector that provides an electrical output signal based on the target chemical. While conveying the light, however, the attenuation region improves the signal-to-noise ratio by attenuating light characterized by the excitation wavelength more than light characterized by the fluorescence region.

20 Claims, 4 Drawing Sheets

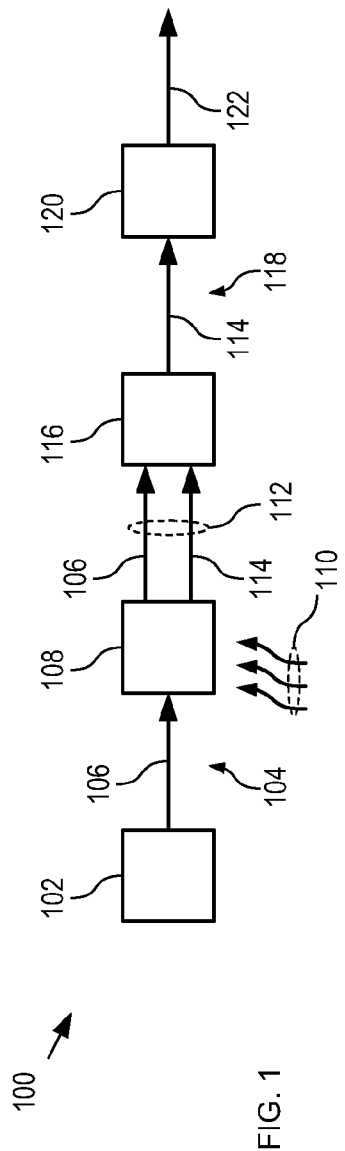
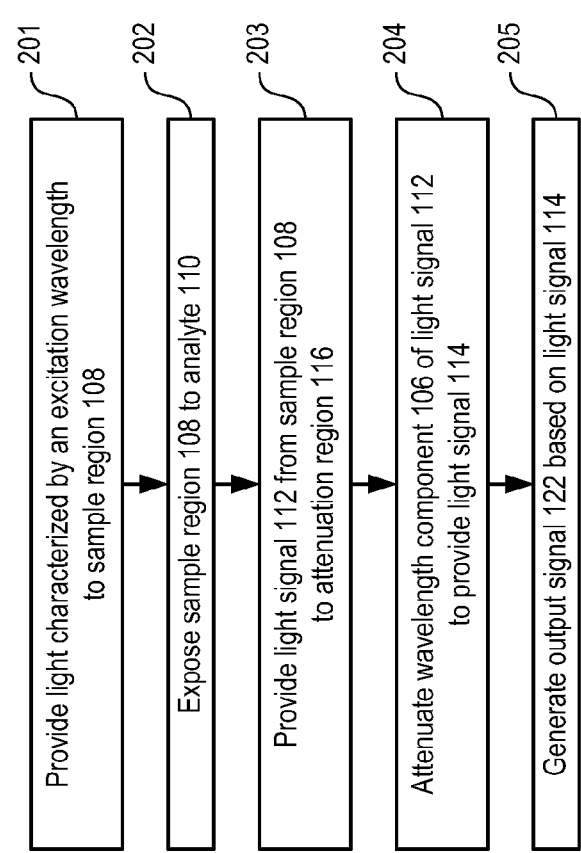
FIG. 1
FIG. 2

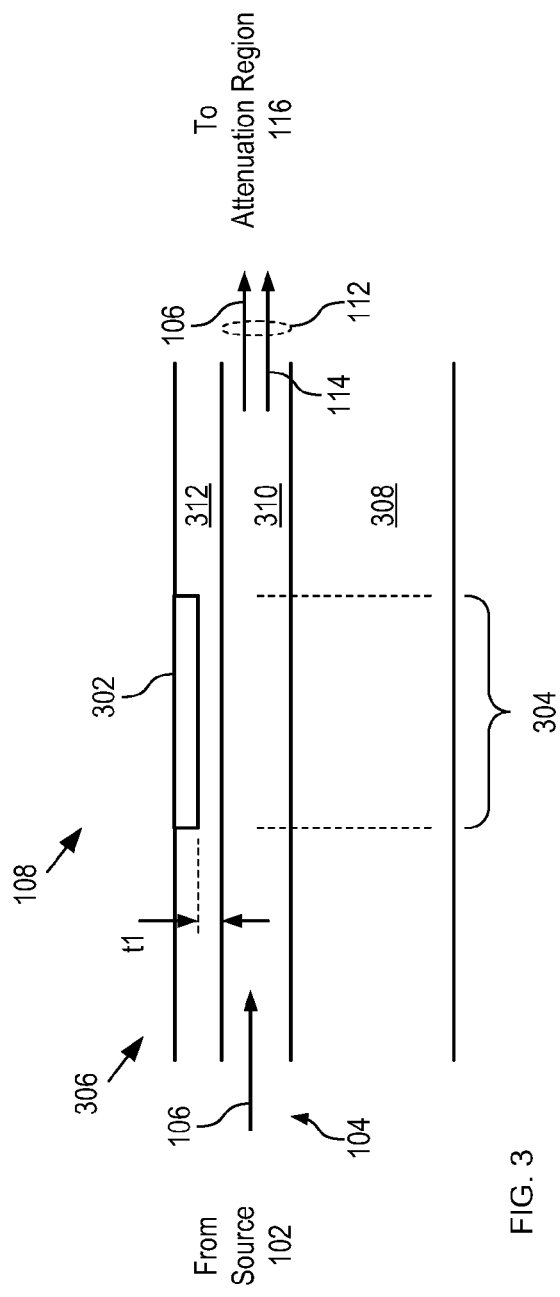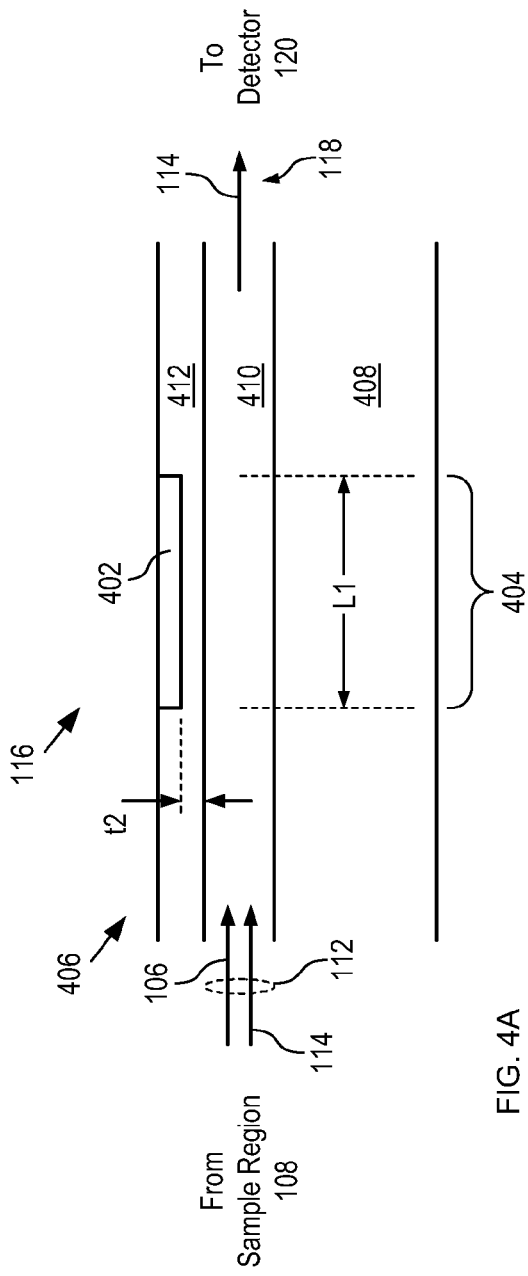

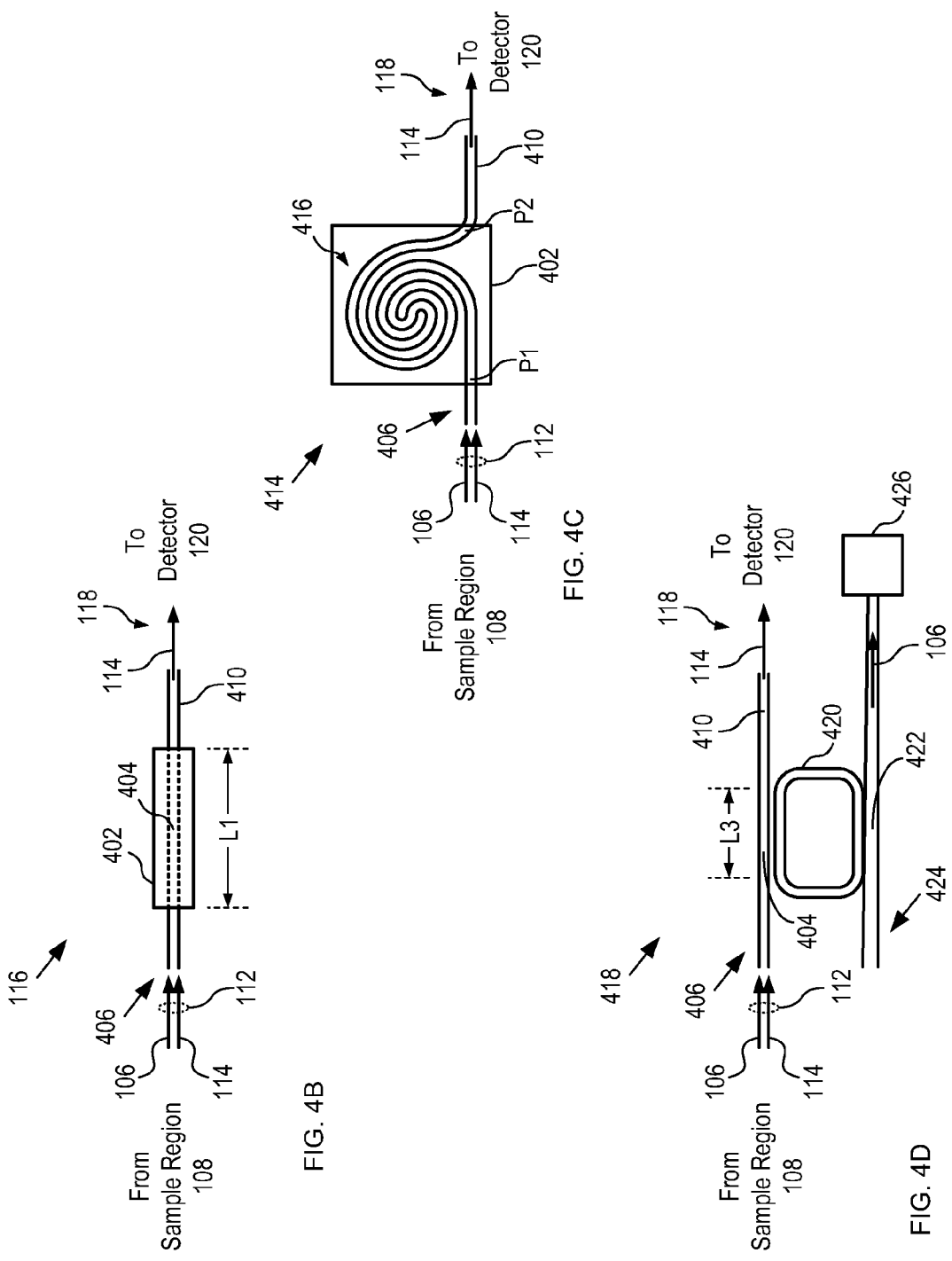

WAVEGUIDE-BASED SENSOR

FIELD OF THE INVENTION

The present invention relates to optical sensors in general, and, more particularly, to fluorescence-based chemical sensors.

BACKGROUND OF THE INVENTION

An ability to form planar lightwave circuits (PLCs) of great complexity within a reasonably small area has led to the development of waveguide-based devices and systems across many applications, such as telecommunications, data communications, radiation sensing, and chemical detection. In telecommunications and data communications systems, for example, PLCs including signal couplers, splitters, wavelength-based routers, and the like, have become seemingly ubiquitous. In chemical detection applications, chemical sensors are widely used to detect the presence and/or concentration of one or more chemicals in applications such as homeland defense, biological and chemical warfare detection systems, and pollution monitoring.

For many devices, more than one wavelength of light is conveyed through the PLC. In wavelength-division multiplexed telecom systems, for example, many different wavelength signals are used, each carrying voice or data information. In chemical sensing applications, for example, different wavelength signals can be used to signify the presence of different chemicals.

In many cases, coupling light between a surface waveguide and an external component, such as an optical fiber or bulk optic element, can be problematic. In telecommunications (and data communications) systems, this problem is mitigated by employing surface waveguides that are single-mode. Single-mode waveguides typically have a very small waveguide core that has a width and height that are substantially the same. As a result, light enters and exits the waveguide with a narrow Gaussian-shape that couples very well with external components.

For chemical sensors, on the other hand, it is often desirable to use a waveguide that has highly asymmetric core layer, wherein the light guiding region is very thin in the vertical dimension (e.g., <1 micron) but very wide horizontally (e.g., >100 microns). Such a waveguide is often referred to as a slab waveguide. Typically, light propagating through the core has an evanescent field that propagates in the cladding layers below and above the core layer. A chemically sensitive material is disposed on the upper cladding layer. When in the presence of a target chemical, the chemically sensitive material alters the evanescent field, which changes a property (e.g., amplitude, phase, etc.) of the light propagating through the core. This change in property constitutes an output signal that is based on the presence of the target chemical. A thin slab waveguide facilitates interaction between the chemically sensitive material and the evanescent field. A wide slab waveguide enables reasonably large sensing regions as well as increasing the amount of light that propagates through the sensing region.

Unfortunately, the light emission of a slab waveguide is non-Gaussian. As a result, beams that enter and exit slab waveguides are poorly matched to external optical elements. Further, slab waveguides are typically multi-mode, which exacerbates these issues.

Many chemical sensors employ a fluorescent material disposed on the top cladding layer. The fluorescent material is "armed" (i.e., stimulated) by an excitation signal comprising light at a first wavelength (i.e., an excitation wavelength) by propagating the excitation signal through the waveguide core. Light in the evanescent field of the excitation signal is absorbed by the fluorescent material, which puts it into an excited state. When exposed to a target chemical, the excited fluorescent material generates an output fluorescence signal at a second wavelength (i.e., a fluorescence wavelength). The target chemical may be an individual chemical, a chemical compound, an analyte, or a biological substance, for example.

Unfortunately, reliable detection of the fluorescence signal can be difficult. Often, the fluorescence signal results in only a slight change in overall intensity of light received at a photodetector. It can be problematic, therefore, to differentiate between noise due to fluctuations of the light source used to provide the stimulative light from the fluorescence signal itself. This low signal-to-noise ratio limits the overall sensitivity of many prior-art fluorescence-based sensors.

In order to improve detection of the fluorescence signal, spectral filters have been used to block the excitation signal at the photodetector. Unfortunately, there is typically only a slight difference between the wavelengths of the stimulative light and the fluorescence signal. As a result, the formation of a filter that passes the fluorescence wavelength but not the excitation wavelength is extremely difficult and typically quite expensive.

In many cases, arrays of fluorescence-based chemical sensor regions formed on a plurality of slab waveguides are used, for example, to enable detection of a plurality of chemicals. Excitation and fluorescence signals are typically coupled into and out of the slab waveguides using lenses or diffraction grating elements. A detector, such as a CCD array, is then used to detect the fluorescence signals from the sensor array. Unfortunately, cross-talk between the regions can make it difficult to differentiate one fluorescence signal from another.

SUMMARY OF THE INVENTION

The present invention enables a chemical sensor having high signal-to-noise ratio. Embodiments of the present invention are particularly suitable for use in environmental chemical sensors, analytical systems, lab-on-a-chip applications, capillary electrophoresis systems, and homeland defense applications. Embodiments of the present invention are also suitable for use in wavelength-division multiplexed (WDM) telecommunications and data communications applications.

The present invention enables the selective attenuation of one wavelength component of a multi-wavelength signal that propagates in a PLC—while the multi-wavelength signal remains in a waveguide of the PLC. Specifically, the present invention comprises an in-line attenuation region in a surface waveguide, wherein the attenuation region selectively removes or attenuates one wavelength component of a multi-wavelength signal as it propagates through the surface waveguide.

An embodiment of the present invention comprises a waveguide comprising a sensing region and an attenuation region. The sensing region comprises a material whose fluorescence at a fluorescence wavelength is enabled by the receipt of stimulative light that is characterized by an excitation wavelength. In the presence of a target chemical, the sensing region provides to the attenuation region a light signal that comprises stimulative light and a fluorescence signal that is based on the target chemical. Stimulative light in the light signal represents output noise that can reduce the sensitivity of the chemical sensor. As the light signal propagates through the attenuation region, its signal-to-noise ratio is improved by the selective attenuation of stimulative light.

In some embodiments, the attenuation region comprises a wavelength-selective absorbing dye that has a higher absorptivity at the excitation wavelength than at the fluorescence wavelength. The dye is optically coupled with a waveguide portion that conveys the light signal through the attenuation region. In some embodiments, the waveguide portion is shaped to facilitate a longer interaction length between the dye and the waveguide portion.

In some embodiments, the attenuation region comprises a resonant element, such as a ring resonator, that has a resonance at the excitation wavelength. As a result, as the light signal is conveyed through the attenuation region, stimulative light is selectively coupled out of the light signal into the resonant element. In some embodiments, the resonant element is also optically coupled with a waveguide that terminates at a beam dump.

An embodiment of the present invention comprises a sensor comprising: a first sensing region that comprises a first material and a first waveguide portion, wherein the first material and the first waveguide portion are optically coupled, and wherein the first material provides a first fluorescence signal that is characterized by a first fluorescence wavelength when exposed to (1) a first target chemical and (2) light that is characterized by a first excitation wavelength; and a first attenuation region, wherein the first attenuation region comprises a second waveguide portion that receives light from the first sensing region, and wherein the first attenuation region attenuates light in the second waveguide portion such that light characterized by the first excitation wavelength is attenuated more than the first fluorescence signal.

BRIEF DESCRIPTION OF THE DRAWINGS

FIG. 1 depicts a schematic diagram of a chemical sensor in accordance with an illustrative embodiment of the present invention.

FIG. 2 depicts a method for sensing a target chemical in accordance with the illustrative embodiment of the present invention.

FIG. 3 depicts a sensing region in accordance with the illustrative embodiment of the present invention.

FIG. 4A depicts a cross-sectional view of an attenuation region in accordance with the illustrative embodiment of the present invention.

FIG. 4B depicts a top view of an attenuation region in accordance with the illustrative embodiment of the present invention.

FIG. 4C depicts a top view of an attenuation region in accordance with a first alternative embodiment of the present invention.

FIG. 4D depicts a top view of an attenuation region in accordance with a second alternative embodiment of the present invention.

DETAILED DESCRIPTION

Figure 5:
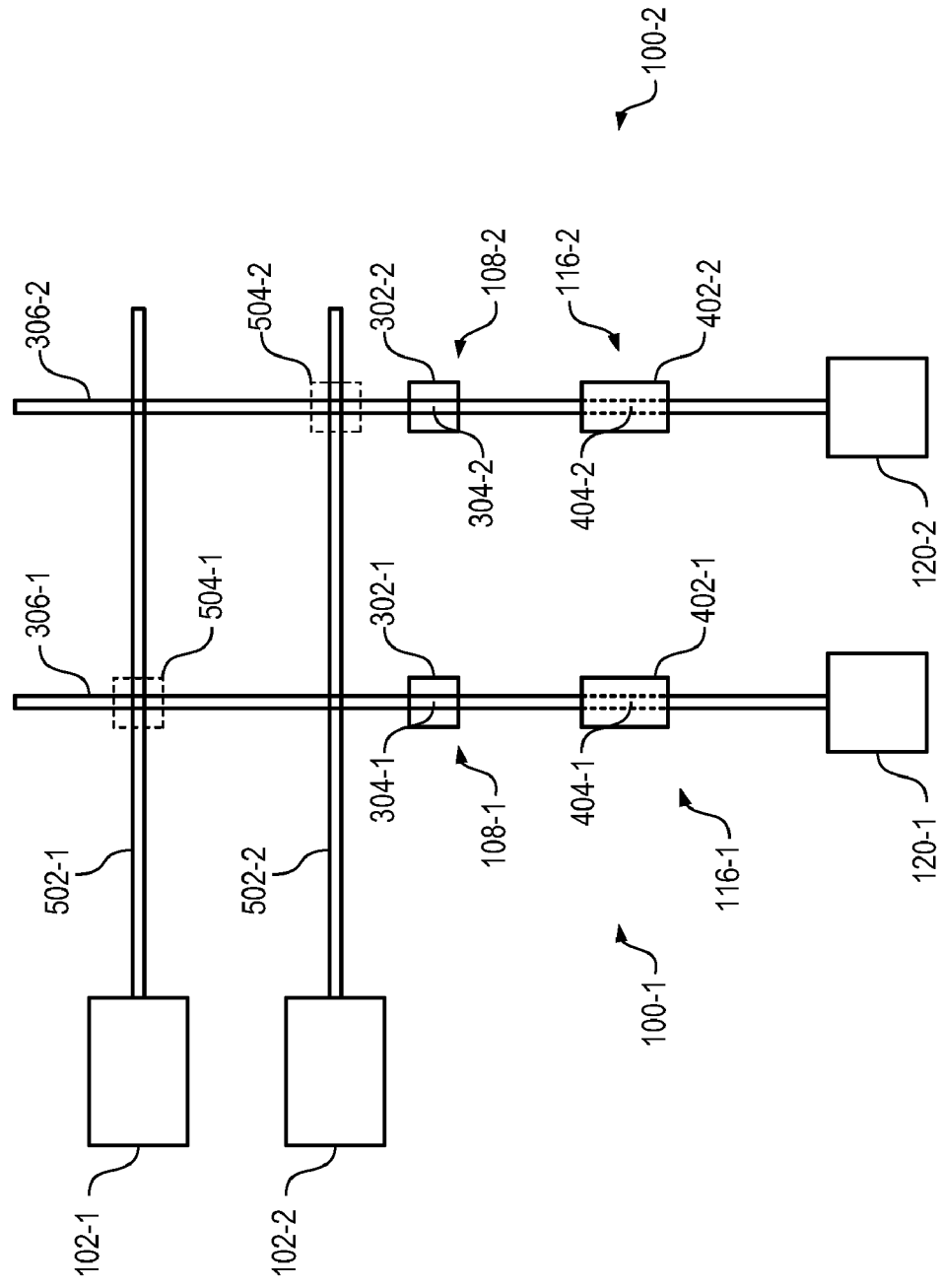
FIG. 5 depicts a top view of an attenuation region in accordance with a third alternative embodiment of the present invention.

FIG. 1 depicts a schematic diagram of a chemical sensor in accordance with an illustrative embodiment of the present invention. Sensor 100 is a scanning sensor that comprises source 102, sensing region 108, attenuation region 116, and detector 120. Sensor 100 provides electrical output signal 122, which is based on the presence of target chemical 110 at sensing region 108.

FIG. 2 depicts a method for sensing a target chemical in accordance with the illustrative embodiment of the present invention. FIG. 2 is described with continuing reference to FIG. 1. Method 200 begins with operation 201, wherein source 102 provides light signal 104 to sensing region 108. Light signal 104 comprises stimulative light 106.

Source 102 is a narrow linewidth light source that provides light signal 104. Light signal 104 comprises stimulative light 106, which is substantially coherent light characterized by a wavelength suitable for enabling fluorescence in sensing region 108 (i.e., an excitation wavelength for fluorescent material 302, described below and with respect to FIG. 3). In some embodiments, source 102 is other than a monochromatic light source, such as a light emitting diode (LED), mercury lamp, and the like. One skilled in the art will recognize, after reading this specification, that source 102 must merely provide light suitable for stimulating the material included in sensing region 108. It will be clear to one skilled in the art, after reading this specification, how to specify, make, and use source 102.

FIG. 3 depicts a sensing region in accordance with the illustrative embodiment of the present invention. Sensing region 108 is an optical transducer that provides a fluorescence signal based on the presence of target chemical 110. Sensing region 108 comprises fluorescent material 302 and waveguide portion 304.

Fluorescent material 302 is a material that provides fluorescence signal 114 by fluorescing at a fluorescence wavelength when exposed to both target chemical 110 and stimulative light 106. In the illustrative embodiment, stimulative light 106 is characterized by a wavelength of 650 nanometers (nm) and fluorescence signal 114 is characterized by a wavelength of 680 nm. These wavelengths are merely representative, however, and one skilled in the art will recognize that fluorescent material 302 can be selected from a wide range of fluorescent materials having excitation wavelengths and/or fluorescence wavelengths other than 650 nm and 680 nm, respectively. It will be clear to one skilled in the art, after reading this specification, how to specify, make, and use fluorescent material 302.

Waveguide portion 304 is a portion of a planar lightwave circuit that comprises surface waveguide 306. Surface waveguide 306 is suitable for conveying stimulative light 106 and fluorescence signal 114. Surface waveguide 306 comprises lower cladding 308, core 320, and upper cladding 322. Surface waveguide 306 has a channel waveguide structure, wherein core 320 is silicon nitride and claddings 308 and 322 are silicon dioxide. The thickness of upper cladding 322 is sufficient to ensure that the evanescent field of stimulative light 106 and fluorescence signal 114 is completely contained within upper cladding 322.

It should be noted that the waveguide structure of waveguide 306 is a matter of design choice. As a result, in some embodiments, waveguide 306 has a waveguide structure other than a channel waveguide structure. The waveguide structure of waveguide 306 can be any suitable waveguide structure, such as a ridge waveguide, planar waveguide, composite-core waveguide, and the like. In some embodiments, the use of a composite-core waveguide affords particular advantage to the present invention as the thickness of the upper cladding layer in such a waveguide is typically thin as compared to other waveguide structures. As a result, it can be easier to format sensing and attenuation regions in its upper cladding. Composite-core waveguides suitable for use with the present invention are described in U.S. Pat. No. 7,146,087, issued Dec. 5, 2006, which is included herein by reference.

One skilled in the art will recognize that materials suitable for use in core 320 and claddings 308 and 322 are not limited to silicon nitride and silicon dioxide. In some embodiments, therefore, materials used in core 320 and claddings 308 and 322 include, without limitation, silicon, glasses, silicon nitride, silicon oxides, III-V materials, II-VI materials, germanium, lithium niobate, polymers, and the like.

In waveguide portion 304, the thickness of upper cladding 322 is reduced to thickness, t1, to facilitate the optically coupling of waveguide portion 304 and material 302. By virtue of the optical coupling of fluorescent material 108 and waveguide portion 304, light signal 204 is evanescently coupled with fluorescent material 108. In some embodiments, upper cladding 322 is removed completely in waveguide portion 304.

Fluorescent material 302 and waveguide portion 304 are optically coupled such that some of the stimulative light propagating in waveguide portion 304 is absorbed by fluorescent material 302. In some embodiments, energy in the evanescent field of the light propagating through the waveguide couples with, and is absorbed by, the fluorescent material.

In some embodiments, source 102 is optically coupled directly with sensing region 108. In some embodiments, source 102 is optically coupled with a different waveguide that is optically coupled with waveguide 306. It will be clear to one skilled in the art, after reading this specification, how to couple light from source 102 into waveguide 306.

Returning now to FIGS. 1 and 2, at operation 202, sensing region 108 is exposed to the target chemical 110. In response to the presence of target chemical 110, fluorescent material 108 emits energy gained from the absorption of some of the light in stimulative light 106 as fluorescence signal 114, which couples into waveguide 306.

At operation 203, attenuation region 116 receives light signal 112. As received by attenuation region 116, light signal 112 comprises fluorescence signal 114 and a portion of stimulative signal 106 that is unabsorbed by fluorescent material 302.

FIGS. 4A and 4B depict a cross-sectional view and top view, respectively, of an attenuation region in accordance with the illustrative embodiment of the present invention. Attenuation region 118 comprises wavelength-selective absorbing dye 402 and waveguide portion 404.

Wavelength-selective absorbing dyes are well-known in the prior art. For example, dyes characterized by narrow absorption-bands have been used in prior-art laser systems as selective wavelength filters. Wavelength-selective absorbing dye 402 (hereafter referred to as "dye 402") is more absorptive for light characterized by the excitation wavelength (i.e., stimulative signal 106) than for light characterized by the fluorescence wavelength (i.e., fluorescence signal 114). Dye 402 is disposed above core 410 in waveguide portion 404.

Waveguide portion 404 is a portion of waveguide 406. Waveguide 406 comprises core 410, lower cladding 408, and upper cladding 412. Waveguide portion 404 has length L1. In waveguide portion 404, upper cladding 412 is thinned to thickness, t2, to facilitate the optical coupling of light signal 112 and dye 402. Since waveguide portion 404 is unshaped (i.e., straight), the interaction length for attenuation region 118 is substantially equal to L1. Waveguide 406 is analogous to waveguide 306 described above and with respect to FIG. 3. Wavelength-selective absorbing dye 402 and waveguide portion 404 are optically coupled such that light signal 112 propagating in waveguide portion 404 interacts with wavelength-selective absorbing dye 402.

Waveguide portion 404 and waveguide portion 304 are optically coupled such that light propagating in waveguide portion 304 is coupled into waveguide portion 404. In some embodiments, waveguide 306 and waveguide 406 are the same waveguide.

At operation 204, attenuation region 116 attenuates stimulative light 106 without significantly reducing the intensity of fluorescence signal 114. As light signal 112 propagates through wavelength portion 404 and interacts with dye 402, dye 402 absorbs stimulative light 106 but not fluorescence signal 114. As a result, stimulative light 106 is substantially removed from light signal 112. After propagating through waveguide portion 404, light signal 112 is passed to detector 120 as light signal 118.

One skilled in the art will recognize that the amount of attenuation of stimulative light 106 in attenuation region 116 is based on the absorptivity of dye 402 for that wavelength, the degree of optical coupling between dye 402 and light signal 112, and the interaction length of attenuation region 116. In some embodiments, stimulative light 106 is not completely removed from signal 112 at attenuation region 116. In some embodiments, some attenuation of fluorescence signal 114 also occurs at attenuation region 116; however, in such embodiments, stimulative light 106 is attenuated more than fluorescence signal 114 so that the signal-to-noise ratio (SNR) of light signal 118 is higher than the SNR of light signal 112.

At operation 205, detector 120 provides electrical output signal 122 based on received light signal 118 from attenuation region 116.

The sensitivity of sensor 100 is based on the ability to discriminate changes in the intensity of light signal 118 as received by a photodetector. Stimulative light 106 represents noise in light signal 118. The present invention, therefore, enables an output signal with higher SNR, and higher sensitivity, than chemical sensors in the prior art.

FIG. 4C depicts a top view of an attenuation region in accordance with a first alternative embodiment of the present invention. Attenuation region 414 comprises dye 402 and waveguide portion 416. Dye 402 and waveguide portion 416 are optically coupled such that light signal 112 propagating in waveguide portion 416 interacts with wavelength-selective absorbing dye 402.

Waveguide portion 416 is a shaped waveguide portion that has a spiral shape. For the purposes of this specification, including appended claims, a "shaped waveguide portion" is defined as a waveguide portion that has a shape other than a substantially straight line. By providing waveguide portion 416 with a non-straight shape, the interaction length between dye 402 and waveguide portion 416 can be increased. For example, the interaction length of attenuation region 414 is equal to the total length of the spiral-shaped waveguide portion 416 from P1 to P2. As a result, a higher attenuation of stimulative light 106 can be achieved within a reasonable footprint. Although in the first alternative embodiment waveguide portion 416 comprises a spiral shape, it will be clear to one skilled in the art, after reading this specification, how to specify, make, and use alternative embodiments of the present invention wherein waveguide portion 416 comprises a shaped waveguide portion that has a shape other than spiral. Suitable shaped waveguide portions include, without limitation, spirals, curves, ovals, and irregular shapes.

FIG. 4D depicts a top view of an attenuation region in accordance with a second alternative embodiment of the present invention. Attenuation region 418 comprises waveguide portion 404, resonant element 420, waveguide portion 422, and beam dump 426.

Resonant element 420 is an optical resonator that has an optical resonance at the wavelength of stimulative light 106. In the second alternative embodiment, resonant element 420 is a racetrack ring resonator; however, it will be clear to one skilled in the art, after reading this specification, that resonant element 420 can comprise any optical resonant device. Resonant element suitable for use in the present invention include, without limitation, disc resonators, ring resonators, tunable resonators, whispering gallery mode resonators, and the like.

Resonant element 420 and waveguide portion 404 are in close proximity over interaction length L3. As a result, stimulative light 106 evanescently couples into resonant element 420 as light signal 112 propagates through waveguide portion 404 of waveguide 406. As a result, at least some of stimulative light 106 is selectively removed from the light signal. In other words, stimulative light 106 is attenuated at attenuation region 418 such that the intensity of stimulative light 106 in light signal 118 is less than its intensity in light signal 112. In some embodiments, stimulative light 106 is completely removed from the light signal thereby leaving light signal 118 with only fluorescence signal 114.

Beam dump 426 receives the stimulative light 106 that has been coupled into waveguide 424, which comprises waveguide portion 422. Beam dump 426 facilitates the removal of the energy of stimulative light 106 from the sensor.

FIG. 5 depicts a top view of an attenuation region in accordance with a third alternative embodiment of the present invention. Sensor 500 comprises two substantially independent chemical sensors 100-1 and 100-2, each of which senses a different target chemical. Sensor 100-1 comprises input waveguide 502-1 waveguide 306-1, sensing region 108-1, attenuation region 116-1, and detector 120-1. In similar fashion, sensor 100-2 comprises input waveguide 502-2 waveguide 306-2, sensing region 108-2, attenuation region 116-2, and detector 120-2.

Each of sources 102-1 and 102-2 provides substantially monochromatic light characterized by an excitation wavelength suitable for sensing regions 108-1 and 108-2, respectively. In some embodiments, sensing regions 108 are stimulated by light having the same wavelength; therefore, sources 102-1 and 102-2 provide light at the same wavelength. In some embodiments, sources 102-1 and 102-2 comprise power couplers that couple light from a single light source into input waveguides 502-1 and 502-2.

Input waveguide 502-1 is optically coupled with waveguide 306-1 at coupler 504-1. As a result, at least a portion of the light conveyed by input waveguide 502-1 is coupled into waveguide 306-1. In similar fashion, input waveguide 502-2 is optically coupled with waveguide 306-2 at coupler 504-2.

Although the third alternative embodiment comprises couplers for coupling waveguides that are oriented orthogonally to one another, it will be clear to one skilled in the art, after reading this specification, how to specify, make, and use, alternative embodiments of the present invention that comprise couplers for coupling waveguides that are oriented with one another in any suitable arrangement. Further, it will be clear to one skilled in the art, after reading this specification, that a sensing region 108 can be co-located with a coupler 504.

Operation of each of sensors 100-1 and 100-2 is analogous to the operation of sensor 100 described above.

In some alternative embodiments, a plurality of sensors 100 is distributed in a two-dimensional arrangement to provide a two-dimensional arrangement of sensing regions 108 that sense the same target chemical. In such embodiments, the collective outputs of the plurality of sensors can be used to develop a two-dimensional map of the distribution of a target chemical across an area. In embodiments wherein the plurality of sensors is monolithically integrated on a single substrate, the collective outputs of the plurality of sensors can provide a two-dimensional map of a target chemical across the substrate.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A sensor comprising:
   a first sensing region that comprises a first material and a first waveguide portion, wherein the first material and the first waveguide portion are optically coupled, and wherein the first material provides a first fluorescence signal that is characterized by a first fluorescence wavelength when exposed to (1) a first target chemical and (2) light that is characterized by a first excitation wavelength; and
   a first attenuation region, wherein the first attenuation region comprises a second waveguide portion that receives light from the first sensing region, a first resonant element that has a resonance at the first excitation wavelength, and a third waveguide portion, wherein the first resonant element couples light characterized by the first excitation wavelength from the second waveguide portion to the third waveguide portion.

2. The sensor of claim 1 further comprising:
   a second sensing region that comprises a second material and a fourth waveguide portion, wherein the second material and the fourth waveguide portion are optically coupled, and wherein the second material provides a second fluorescence signal that is characterized by a second fluorescence wavelength when exposed to (1) a second target chemical and (2) light characterized by a second excitation wavelength; and
   a second attenuation region, wherein the second attenuation region comprises a fifth waveguide portion that receives light from the second sensing region, and wherein the second attenuation region attenuates light in the fifth waveguide portion such that light characterized by the second excitation wavelength is attenuated more than the second fluorescence signal.

3. The sensor of claim 2 wherein the first excitation wavelength and the second excitation wavelength are the same wavelength.

4. A method for sensing a target chemical, wherein the method comprises:
   providing a first light signal from a sensing region comprising a first waveguide portion, wherein the first light signal comprises light characterized by an excitation wavelength and a fluorescence signal that is characterized by a fluorescence wavelength, and wherein the fluorescence signal is based on the target chemical;
   receiving the first light signal at an attenuation region comprising a second waveguide portion, wherein the second waveguide portion receives the first light signal from the first waveguide portion; and
   attenuating the first light signal in the attenuation region, wherein the attenuation region attenuates light characterized by the excitation wavelength more than it attenuates the fluorescence signal, and wherein the attenuation region attenuates the first light signal by selectively coupling light characterized by the excitation wavelength from the second waveguide portion into a third waveguide portion.

5. The method of claim 4 wherein the light characterized by the excitation wavelength is coupled from the second waveguide portion into the third waveguide portion via a resonant element having a resonance at the excitation wavelength.

6. The sensor of claim 1 further comprising:
a first waveguide, wherein the first waveguide comprises the first waveguide portion and the second waveguide portion; and
a second waveguide, wherein the second waveguide is optically coupled with the first waveguide, and wherein the second waveguide is optically coupled with a source that is dimensioned and arranged to provide light characterized by the first excitation wavelength.

7. The sensor of claim 1 further comprising a beam dump, wherein the beam dump is dimensioned and arranged to remove light characterized by the first excitation wavelength from the third waveguide portion.

8. The sensor of claim 2 further comprising:
a first waveguide, wherein the first waveguide comprises the first waveguide portion and the second waveguide portion; and
a second waveguide, wherein the second waveguide comprises the third waveguide portion and the fourth waveguide portion.

9. The sensor of claim 8 further comprising a third waveguide, wherein the third waveguide is optically coupled with a source that is dimensioned and arranged to provide light characterized by the first excitation wavelength, and wherein the third waveguide is optically coupled with each of the first waveguide and the second waveguide.

10. The sensor of claim 2 wherein the second attenuation region further comprises a second resonant element that has a resonance at the second excitation wavelength, and a sixth waveguide portion, wherein the second resonant element couples light characterized by the second excitation wavelength from the fifth waveguide portion to the sixth waveguide portion.

11. The method of claim 4 further comprising removing at least a portion of the light characterized by the excitation wavelength from the third waveguide portion via a beam dump.

12. The method of claim 4 further comprising coupling a second light signal from a first waveguide to a second waveguide that comprises the first waveguide portion, wherein the second light signal comprises light characterized by the excitation wavelength.

13. A sensor comprising:
a substrate comprising a plurality of sensing regions and a plurality of attenuation regions, each of the plurality of sensing regions being optically coupled with a different one of the plurality of attenuation regions, wherein the plurality of sensing regions are arranged in a two-dimensional arrangement;
the plurality of sensing regions, each sensing region providing a fluorescence signal that is characterized by a fluorescence wavelength when exposed to (1) a target chemical and (2) light that is characterized by an excitation wavelength; and
the plurality of attenuation regions, each attenuation region comprising;
(i) a first waveguide portion;
(ii) a second waveguide portion; and
(iii) a resonant element that is dimensioned and arranged to be resonant at the excitation wavelength, wherein the resonant element couples light characterized by the excitation wavelength from the first waveguide portion to the second waveguide portion;
wherein the plurality of sensing regions are arranged in a first arrangement.

14. The sensor of claim 13 further comprising a plurality of detectors, each detector of the plurality of detectors being optically coupled with a different attenuation region of the plurality of attenuation regions.

15. The sensor of claim 13 further comprising a first waveguide, wherein the first waveguide is optically coupled with a source that is dimensioned and arranged to provide light characterized by the excitation wavelength, and wherein the first waveguide is optically coupled with each of the plurality of sensing regions.

16. The sensor of claim 13 wherein at least one of the plurality of resonant elements comprises a ring resonator.

17. The sensor of claim 13 wherein at least one of the plurality of resonant elements comprises a racetrack ring resonator.

18. The sensor of claim 13 wherein at least one of the plurality of resonant elements comprises a disc resonator.

19. The sensor of claim 13 wherein at least one of the plurality of resonant elements comprises a whispering gallery mode resonator.

20. The sensor of claim 13 wherein at least one of the plurality of resonant elements comprises a tunable resonator.

* * * * *